United States Patent [19]

Stellmacher et al.

[11] Patent Number: 5,088,690

[45] Date of Patent: Feb. 18, 1992

[54] ELECTRODE HOLDER FOR IMMERSION-TYPE, FLOW-TYPE AND ATTACHMENT-TYPE MEASURING SYSTEMS IN ANALYTICAL CHEMISTRY

[75] Inventors: Klaus Stellmacher, Oberreichenbach; Hans J. Oppermann, Gemmrigheim, both of Fed. Rep. of Germany

[73] Assignee: Conducta Gesellschaft Fur Meb-Und Regeltechnik MBH & Co., Gerlingen, Fed. Rep. of Germany

[21] Appl. No.: 565,375

[22] Filed: Aug. 9, 1990

[30] Foreign Application Priority Data

Aug. 18, 1989 [DE] Fed. Rep. of Germany ....... 3927282

[51] Int. Cl.$^5$ .................... G01N 27/28; F16K 3/24
[52] U.S. Cl. .................. 251/309; 422/82.01; 422/103
[58] Field of Search .............. 251/309; 422/82.01, 422/82.02, 82.03, 82.04, 103

[56] References Cited

FOREIGN PATENT DOCUMENTS 0271764 6/1988 European Pat. Off. .
2557542 1/1980 Fed. Rep. of Germany .
WO86/07151 12/1986 PCT Int'l Appl. .

Primary Examiner—Gerald A. Michalsky
Attorney, Agent, or Firm—Darby & Darby

[57] ABSTRACT

In connection with an electrode holder for immersion-type flow-type and attachment-type measuring systems in analytical chemistry, in particular for pH, conductivity, oxygen and chloride measurements, or the like, comprising an outer pipe in which an inner pipe carrying the measuring probe is supported in axially sliding relationship, and a stopcock blocking the supply of measuring agent by means of a plug of the stopcock when the inner pipe is retracted from the measuring agent it is proposed to leave the plug open on one side in the area of its passage channel and to have a remaining rear wall of the passage channel facing the supply opening of the measuring agent.

6 Claims, 3 Drawing Sheets

ELECTRODE HOLDER FOR IMMERSION-TYPE, FLOW-TYPE AND ATTACHMENT-TYPE MEASURING SYSTEMS IN ANALYTICAL CHEMISTRY

BACKGROUND OF THE INVENTION

The present invention relates to an electrode holder for immersion-type and flow-type measuring systems in analytical chemistry, according to the preamble of claim 1.

It is frequently an indispensable necessity in analytical chemistry that chemical sensors of immersion-type or flow-type measuring systems employed, for example, for the continuous monitoring of biological or chemical processes by corresponding measurements of the analytical parameters of a liquid measuring agent, be calibrated or cleaned. On the other hand, however, these processes are troublesome and time-consuming as in order to permit such operations to be carried out, the respective measuring electrodes, for example, measuring systems for pH, conductivity, oxygen or chlorine measurements, or the like, must be retracted from the measuring agent under process conditions, without there always being the possibility to interrupt the process for this purpose, to drain the measuring agent or to completely block a pipeline for passage by the measuring agent.

It has, therefore, been known (WO 86/07151) to arrange the transducer probe, being part of the measuring system, in a guiding mechanism by which the sensor is held and guided between an operating position and a servicing position, and to provide in addition a stopcock by means of which the area previously occupied by the transducer is shut off relative to the measuring agent when the transducer has been retracted. Consequently, it is the basic principle of such transducer probes that in order to permit any necessary calibration or cleaning operations, or to enable the electrode to be watered for a predetermined period of time, for example, the design of the electrode holder, which reaches into the pipeline containing the measuring agent or into the reaction tank, is selected in such a way that the electrode can be moved from an immersed position into a retracted or withdrawn position, in which case the previously existing connection to the measuring agent is shut off hermetically in a suitable way. It has been known in this connection (DE-PS 2 557 542) to incorporate the electrode in ball valves performing the function of the stopcock, which valves then separate the electrode from the measuring agent when the latter is retracted, thus making it accessible for the cleaning or calibration agents or for other treatments.

It has also been known in this connection (European Patent Application 0271764) to provide around the active electrode area a calibration space, especially for pH electrodes, which is open in the operating position and closed in the servicing position. This is achieved by means of a sleeve mounted for longitudinal displacement in a sliding guide of the electrode holder and accommodating the electrode carrier in its interior, there being further provided first control means by which longitudinal channels are opened and connected to valve connections in the control head of the fittings, which open into the calibration space, so that the latter can be supplied with the respective agent, such as water/cleaning agent, buffer solution, or the like, in the servicing position, while in the operating position all annular spaces, sealing areas and openings of the valve are under the effect of compressed air acting from the inside to the outside.

If the electrode holders use stopcocks, the stopcock bodies of the valve may consist of cylindrical, spherical or conical plugs, which then lead to the advantages and drawbacks typical for these different types.

If ball or cylinder valves are used in such shut-off devices, it is in any case a particularly serious disadvantage that the respective measuring electrode or probe first has to be fully withdrawn from the rotary area of the plug before the connection to the measuring agent, which may contain very disturbing and contaminating substances, can be interrupted by rotating a cylinder-shaped or ball-shaped stopcock element (plug). This leads, however, to contaminated dead spaces in the area of the stopcock element, a fact which may cause considerable trouble, in particular if the agents contain abrasive substances or tend to deposit. Further, it is a problematic aspect that the measuring electrode, and especially its sensitive forward conical portion has to be fully withdrawn, i.e. removed, from the rotary area of the plug before the plug can be rotated, as otherwise the plug, which separates the measuring electrode from the agent, may shear off the sensitive electrode tip, for example, and destroy the measuring system in its entirety. In view of this aspect, it has been known to arrange a suitable impact protection in the forward area of the measuring probe, for example in the form of impact-protection bolts or impactprotection cages, so as to prevent the electrode from being sheared off by the stopcock. However, such protections tend again to collect dirt and lint and this to a degree which may finally lead to complete blocking of the system.

Another disadvantage resides in the fact that a considerable displacement is required to remove the electrode, which together with its sliding holder passes through the plug opening, fully from both the measuring agent and the area of rotation of the plug. This rather long displacement either consumes free working space in the area of the measuring agent, or requires the provision of additional space through expensive constructional measures as the measuring probe must be retracted to the rear the full length by which it dips into the measuring agent.

Ball valves, in particular, provide additional problems being mounted in more or less floating relationship and being symmetrized by suitable packings in the housing of the stopcock, so that ball valves are less suited in connection with those modifications for which the following invention can be used with particular advantage.

Now, it is the object of the present invention to design the area of the stopcock of an electrode holder in such a way that no disadvantageous dead spaces tending to be contaminated or to give other trouble are produced during transfer of the plug from one position to the other.

ADVANTAGES OF THE INVENTION

The invention achieves this object with the aid of the characterizing features of the main claim and provides the advantage that the opening provided on one side of the plug of the stopcock makes it possible to rinse in a single operation both the electrode and the dead spaces which otherwise would be shut off from the electrode cleaning area in the retracted position so that cleaning thereof would be possible only by separate cleaning steps, if such can be implemented and are rendered necessary by the measuring agent. Any fibrous materials (paper or other textile materials) can simply be pushed off during this operation, there being no transverse bores in the plug area, as in the case of protective cages.

Another advantage is seen in the fact that it is no longer necessary to retract the electrode a length as important as in the case of the design known heretofore, but that the electrode may remain in the area of the plug of the stopcock, which leads to a considerable reduction of the length of displacement, it being nevertheless ensured under all conditions that the plug cannot damage the electrode during its transfer motion, and this even in the absence of a protective cage or protective bolt.

The features specified in the subclaims permit advantageous further developments and improvements of the electrode holder specified by the main claim. According to a particularly advantageous feature, the electrode present in the plug space during the transfer motion of the plug is automatically pushed into its final position due to a curve shape produced by the plug so that any damage to the electrode is definitely excluded. The movements performed in this connection may be produced by a pneumatic, hydraulic, electric or any other drive, or manually. A particularly advantageous solution is achieved when the stopcock body consists of a cylindrical plug as then the sealing aspect can be managed more easily. Such a solution also provides the additional advantage that in the case of cylindrical plugs an improved sealing effect can be achieved by an O-ring which is supported by the plug itself and which, when the plug is rotated correspondingly, seals the supply opening to the measuring agent, together with and in addition to other radial seals provided on the two end portions of the cylindrical plug, thereby shutting off the outer space and preventing any penetration of the measuring agent. In addition, a cylindrical plug offers the advantage, by comparison with a ball valve, that a floating seat can be avoided. In addition, it must be considered above all that a cylindrical plug can be produced more easily from any type of suitable semi-finished material, while ball valves can be produced only from special materials, and in addition the production of the spherical shape is rather cost-consuming. However, it should be noted that, generally, spherical plugs are also suited for implementing the present invention, though cylindrical plugs may be employed with greater advantage.

BRIEF DESCRIPTION OF THE DRAWING

One embodiment of the invention will be described hereafter in more detail with reference to the drawing in which

FIG. 2 shows a similar longitudinal section through the embodiment illustrated in FIG. 1, but turned by 90° about the longitudinal axis, while

DESCRIPTION OF THE EMBODIMENTS

The basic idea of the present invention lies in the fact that one side of the—preferably—cylindrical plug is left open so that the flow or passage channel formed by that stopcock body is not closed on one side so that the forward portion of the measuring probe, i.e. the electrode tip, for example, may remain in position on that same side, which leads to a shorter stroke and provides the possibility, with the supply of measuring agent tightly sealed by the other closed side of the plug, to clean the dead spaces and the electrode simultaneously, to apply to them buffer or calibration solutions, or simply to water them or to carry out any other manipulations in this area, the latter being now freely accessible.

Figure 1:
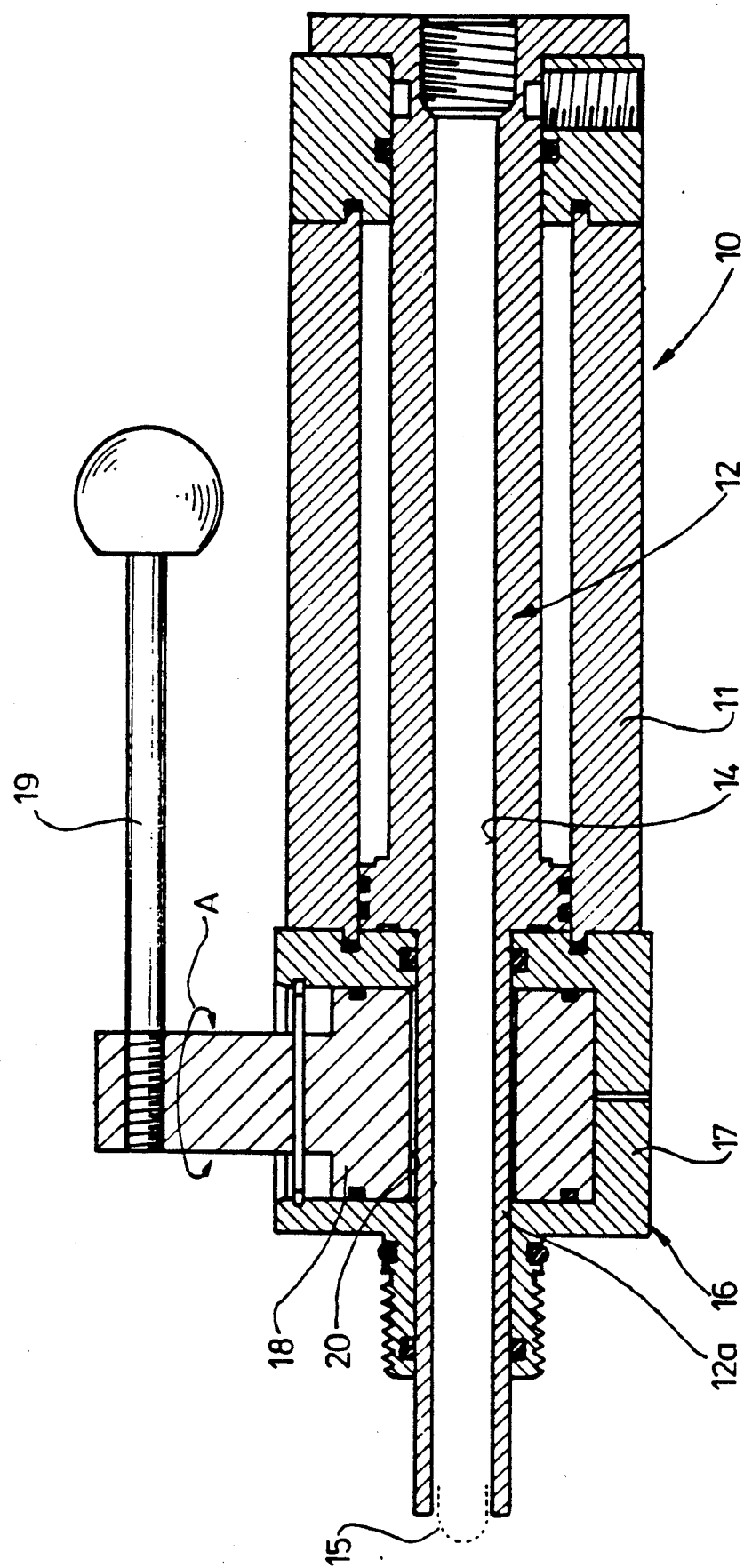
FIG. 1 shows a longitudinal section through a first embodiment of an electrode holder using a cylindrical plug as stopcock.
Figure 2:
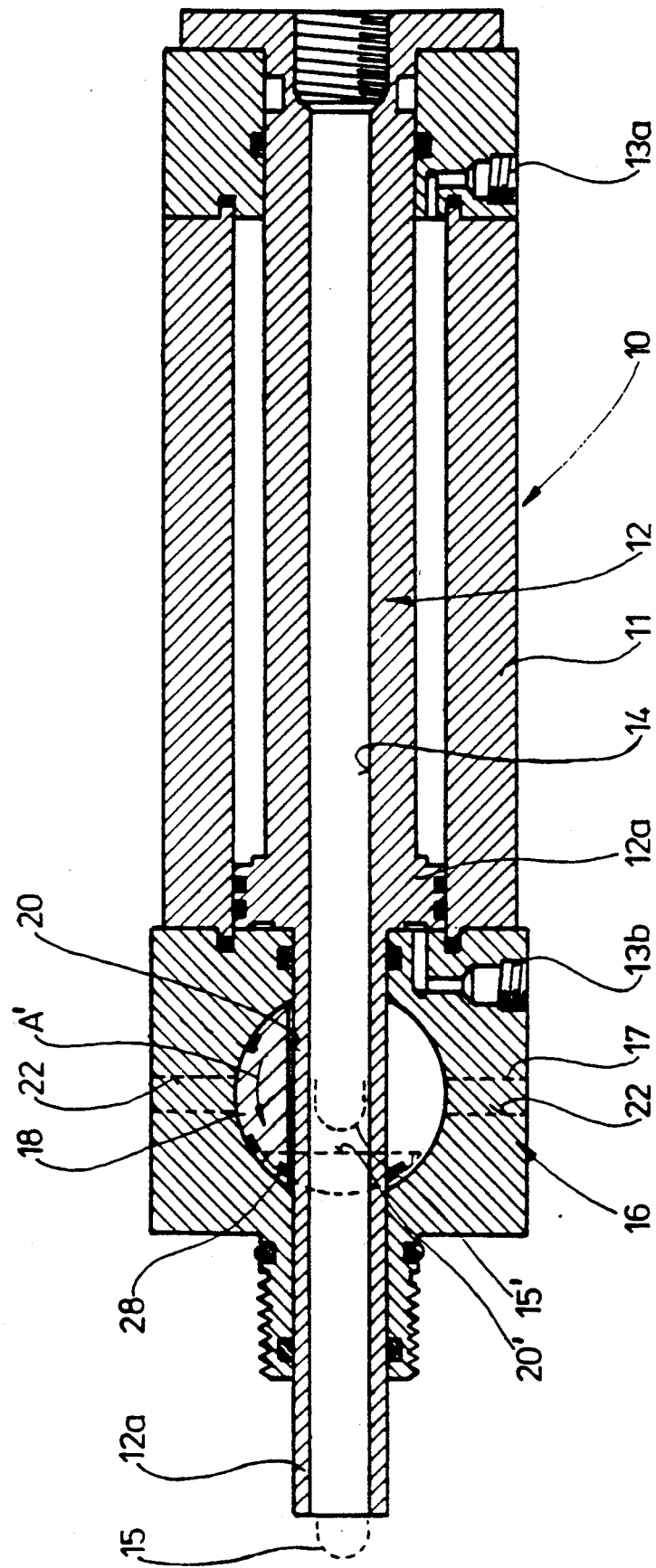
Figure 3:
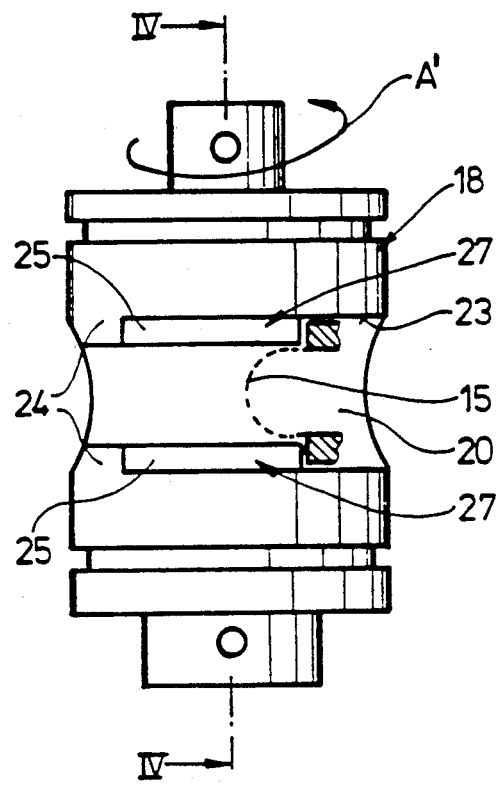
FIGS. 3, 4, 5 and 6 show a side view, a section along line IV—IV in FIG. 3, a side view opposite to that of FIG. 3, and a section along line IV—IV, respectively, of the cylindrical plug of the stopcock, in the stated order.

Regarding now FIGS. 1 and 2, one can see an electrode holder 10, a preferably cylindrical outer pipe 11 of the electrode holder, and an inner pipe 12 which is mounted for longitudinal displacement in the outer pipe and which is simultaneously intended to receive the measuring probe proper. Generally, the type and structure of the inner and outer pipes and of the relative axial displacement between the two pipes—which in the case of the present embodiment may also be effected in a controlled manner and, accordingly, also automatically—may be selected at desire, the invention being related essentially to the design in the area of the stopcock. However, in the representation of FIG. 2, pressure agent inlets and outlets 13a, 13b can be seen through which a piston-like wider portion 12a of the inner pipe can be subjected, preferably in a valve-controlled manner, to the action of the pressure agent for being moved into a downward position, as illustrated in FIGS. 1 and 2, or to an upward position, which movement then causes the hollow piston-like extensions, which are provided on both sides and which are formed as a single piece with the extension 12a, to follow this movement, the measuring system being accommodated in the central bore 14 of the inner pipe 12. While the measuring system is not shown in the drawing, its slightly projecting tip, which may be the glass tip of a pH electrode, or any other type of measuring probe, is illustrated in FIG. 1 by dotted lines and indicated by reference numeral 15. FIG. 3 shows this electrode tip in a similar manner, so that one can form an idea of the mechanism underlying the present invention, which will now be described in more detail.

The inner and the outer pipes 11 and 12, therefore, form sort of a piston-and-cylinder unit ensuring the axial relative movement of the inner pipe 12, together with the measuring probe—this term will be consistently used hereafter to describe the measuring system—while the lower end of the outer pipe 11 forming the cylinder carries the stopcock 16 which in its turn consists of an outer housing 17 and the stopcock 18 proper, as shown in the drawing in a simplified manner. In the illustrated embodiment, the stopcock 18 is formed by a cylindrical plug which—to simplify the understanding in the present case—is actuated by an outer hand lever 19 which, when turned in the direction of the double arrow A, causes the cylindrical plug 18 to perform a rotary movement.

In the illustrated position, the lower extension 12a of the inner pipe 12 passes through the central passage bore or passage channel 20 of the cylindrical plug 18 so that the illustrated measuring system, with the measuring probe in its lower position, occupies the position in which it is ready to operate, as can be seen in the drawing. A plurality of seals, which are not referenced individually, ensure that the cylinder-and-piston area and the upper connections of the measuring probe are either outside the measuring agent or in any case prevented from getting into contact with the latter.

The main point of the present invention is seen in the particular design of the—in the present case cylindrical—plug of the stopcock, the sectional view of FIG. 1 being suited best to illustrate the relationships. It will be seen that the central passage channel 20, which is passed by the extension 12a of the inner pipe, together with the shaft of the measuring probe, is open on one side, namely at 21 so that the plug assumes a generally U-shaped cross-section in the described figure.

Now, the open area 21 has the effect that the measuring probe, together with its tip 15, may remain in the area of the plug also in its retracted position, which hereafter will be generally described as servicing position, and has to be retracted only a length corresponding to the initial position illustrated in FIG. 3, before the rotary movement of the plug begins. An additional particularity that will be noted in the present case consists, however, of safety webs provided on both sides in the open area of the plug, as a security measuring against shearing off of the tip of the measuring probe and as a means for pushing the latter automatically in outward direction a sufficient length—a mechanism which will be described hereafter.

For, if the inner pipe 12 is retracted—in upward direction in FIGS. 1 and 2—with the plug 18 being open on one side, then the forward tip of the measuring probe may well remain in the area of the plug acting as stopcock body-as illustrated in FIG. 3—there being no wall portion that may shear off the probe tip or the measuring probe.

Now, when the cylindrical plug—as shown in the representation of FIG. 2—is turned from the position shown in full lines in the direction indicated by arrow A' into the position indicated by dashed lines, for blocking the supply of measuring agent, with the inner pipe 12 in the retracted position, it will be appreciated at once that the tip 15 of the measuring probe may well remain in the retracted position 15' indicated by dashed lines in FIG. 2, without any risk that the tip of the measuring probe might be damaged by the rotating plug.

On the other hand, the passage channel to the measuring agent is shut off efficiently in downward direction by the remaining portion of the plug wall, the passage channel—which now extends in the transverse direction—now occupying the position 20' in which the channel and the tip of the measuring probe 15' can be cleaned and rinsed in any desired manner and the measuring probe can be re-worked, watered, calibrated, or the like. If course, it is also possible in this case, if desired and as indicated at 22, to provide the housing 17 of the stopcock with additional transverse channels through which convenient rinsing, buffer or calibration solutions, or other agents can be supplied. The latter can efficiently reach all dead spaces in the area of the stopcock and also the tip of the measuring probe without any need to retract the measuring probe fully from the area of the stopcock, which would require a much longer stroke.

Figure 4:
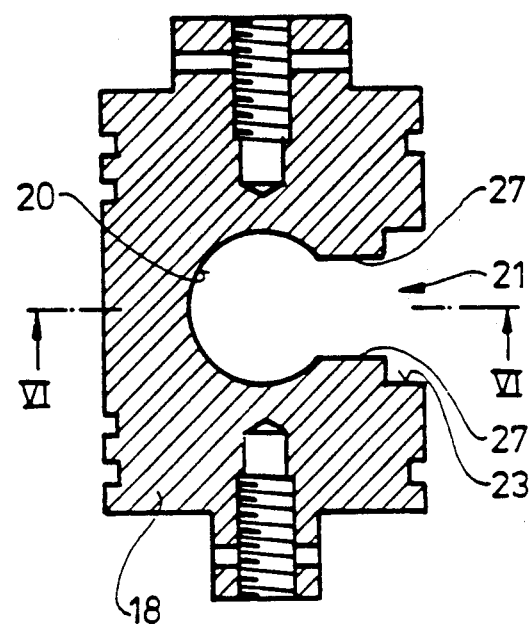
Figure 6:
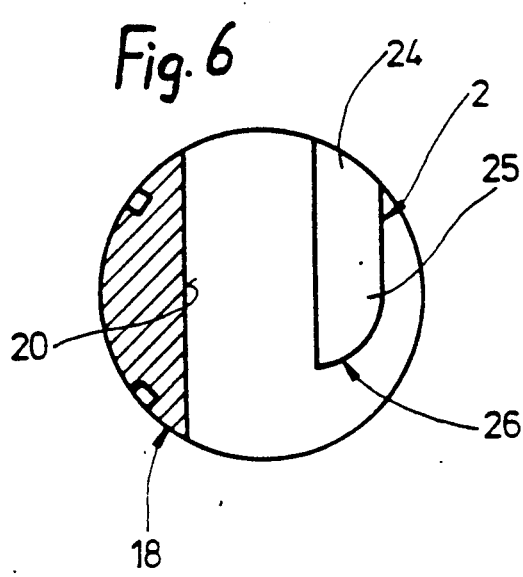

According to another preferred embodiment, which has been shortly referred to before, the removed wall portion of the cylindrical plug extends up to the full height of the diameter of the passage channel 20 only on one side, namely at 23 (compare FIGS. 3 and 4), while at the upper left and upper right of FIG. 3 a wall portion, reduced by the distance B, has been left in place on both sides which then progressively flattens out, as indicated at 25, until the curve shape forming shoulders on both sides disappears-as can be seen best in FIG. 6.

The mechanism provoked by this arrangement is likewise illustrated best by the representation of FIG. 3, the latter showing the initial rotary position of the cylindrical plug 18, in combination with the retracted initial position which the tip 15 of the probe assumes in connection with the inner pipe extension 12a before the plug is rotated into its blocking position. It will be readily appreciated that the beginning rotary movement of the plug by 90°, from the position illustrated in FIG. 3 into the cross-sectional position illustrated in FIG. 4, in the direction of arrow A', will cause the forward or—in FIGS. 1 and 2—lower end wall of the inner pipe extension to abut against the initial curve portion 26 of the upper and lower guide web 27 in the free passage of the plug 18, while the sensitive probe tip 15 projects into the free space of the passage channel in a protected manner. As the plug is then rotated, the guide webs 27 push the tip of the measuring probe automatically back a further length to guarantee that the rotary movement of the plug itself will ensure under any circumstances and even if erroneous displacements should occur that the tip of the measuring probe cannot suffer any damage. This is ensured by the fact that the measuring probe is pushed back forcedly by the stopcock body so that the probe cannot possibly remain in a position in which it may be endangered.

Figure 5:
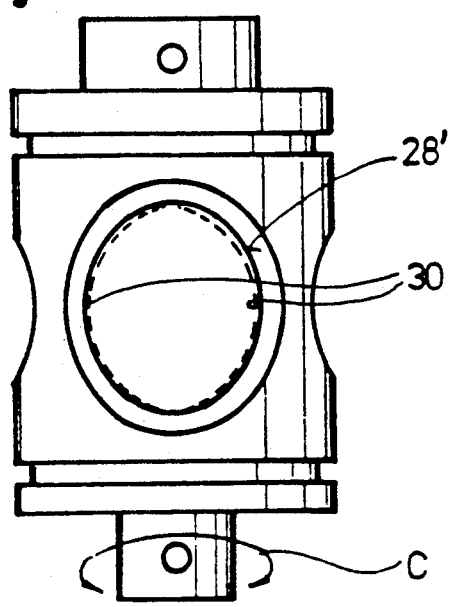

It should be noted in this connection that an annular seal 28 is provided on the remaining rear face of the plug, i.e. the surface which faces the measuring agent supply when the plug occupies the blocking position illustrated in FIG. 2, the said seal being accommodated in a groove 28' which follows an elliptical curve and, at the same time, the cylindrical curvature of the plug. The described receiving groove 28 can be produced by applying a milling cutter on the cylindrical surface illustrated in FIG. 5 from above, i.e. in a direction vertical to the drawing plane, and causing the cutter to move along the oval shape of the elliptical annular groove 28'. Simultaneously, the plug body may perform a swinging movement in the direction indicated by double arrow C so that slight undercuts will be obtained on both sides of the groove 28'—as indicated in dashed lines at 30—so that an O ring placed in the groove will be safely retained and will be prevented from getting dislodged from its groove also during the transfer movements from the blocking into the open position, and vice versa, when the O ring has to pass the supply opening for the measuring agent.

All the features described in the specification, the following claims and the drawing may be essential to the invention either individually or in any combination thereof.

We claim:

1. An electrode holder for immersion-type measuring systems for measuring the parameter of an agent comprising an outer pipe, an inner pipe adapted to carry a measuring probe supported in axially sliding relationship to said outer pipe for movement toward and away from the agent, and a stopcock operable to block the supply of agent when the inner pipe is retracted from the agent, said stopcock comprising a plug having a channel receiving said inner pipe in sliding engagement therethrough, and a passage extending from said channel to the surface of said plug positioned to receive the retracted inner pipe when said stopcock is moved to the blocking position.

2. An electrode holder according to claim 1, wherein said plug of said stopcock is of cylindrical form.

3. An electrode holder according to claim 2, wherein said stopcock includes a housing having a passage open to the agent, and said channel is defined by walls, and an annular seal in one of said walls for sealing said agent passage when said stopcock is moved to the blocking position.

4. An electrode holder as in claim 3, wherein said plug is provided with an annular groove, and said annular seal comprises an O-ring received in said annular groove, said annular groove having undercuts therein to secure the seal in place.

5. An electrode holder according to claim 1, and at least a guide web in said plug sized and positioned to engage the end of said measuring probe when said plug is moved to said blocking position to position the probe carried by said inner pipe out of the path of travel of the walls defining said channel.

6. An electrode holder according to claim 5, and at least two opposed guide webs in said plug, each of said guide webs tapering inwardly from the outer surface of said plug to said channel and having a curved surface engageable with the edge of said inner pipe when said plug is moved to the blocking position, the spacing between said webs being in excess of the width of the tip of a measuring probe received therebetween.

* * * * *